June 4, 1968 H. C. SWIM ETAL Plant Pat. 2,815
ROSE PLANT
Filed Jan. 10, 1967
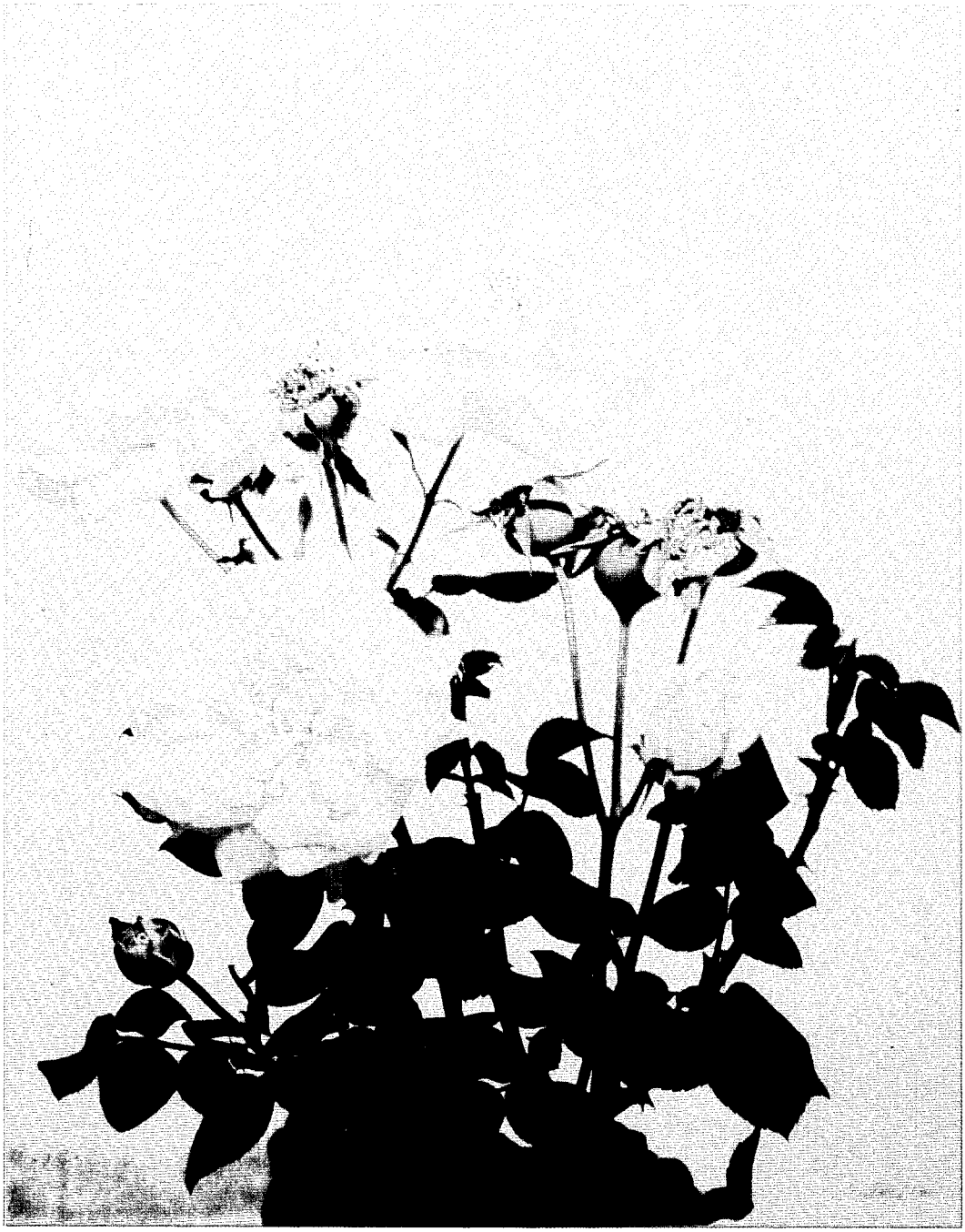

United States Patent Office

Plant Pat. 2,815
Patented June 4, 1968

2,815
ROSE PLANT

Herbert C. Swim, Ontario, and O. L. Weeks, Chino, Calif., assignors, by mesne assignments, to O. L. Weeks, doing business as Weeks Wholesale Rose Grower, Chino, Calif.

Filed Jan. 10, 1967, Ser. No. 608,464
1 Claim. (Cl. Plt.—24)

The present invention relates to a new and distinct variety of rose plant of the floribunda class. The plant is a dwarf bush seedling, well adapted for garden decoration. The variety was originated by us by crossing Arlene Francis (Plant Patent No. 1,684) with an unnamed seedling of Circus × Sweet Talk. As a result of this breeding, we have asexually produced a new and improved rose variety having the following unique characteristics which are outstanding therein, and which, taken together, distinguish it from its partents as well as from all other varieties of which we are aware:

(1) The bright greenish-yellow color of the flowers.

(2) The large size of the flowers, considering that the plant is of the floribunda class.

(3) Persistence of the flower color as the flower ages.

(4) The form of the buds and the flowers, which are short-pointed to urn-shape at the beginning, and progress through a high-centered opening stage to the full bloom, which has double petalage but with the stamens not completely hidden.

(5) The lark green color of the leaves which are of normal quantity and moderately heavy-leathery in texture or substance.

(6) The nearly continuous bloom during the growing season.

(7) The relatively low-growing habit of the plant.

In comparison with the seed parent, the following differences may be noted:

(1) A great may of the flowers of the new variety are produced in clusters, although some of the flowers are produced on individual stems. It is properly classed as a floribunda. In contrast, Arlene Francis is classified as a hybrid tea rose, and all of its flowers are produced on individual stems except for those which are a part of the basal growth or of an especially strong growth.

(2) The new variety is substantially lower growing than its seed parent.

(3) The flowers of the new variety, although golden in color, have a distinctly greenish hue, which could more appropriately be described as greenish-yellow, whereas the flowers of Arlene Francis are golden yellow.

(4) The flowers of the new variety often have as many as thirty-eight petals, and in addition, up to possibly fifteen petaloids, whereas the Arlene Francis rose has no more than about thirty petals in its flowers with few if any petaloids, and its center petals are much broader than the center petals of the new variety.

(5) The flowers of the new variety are only occasionally larger than about 3½" in diameter, whereas the flowers of the Arlene Francis rose are frequently as large as 5" in diameter.

This new variety is distinct from its pollen parent, the unnamed and unintroduced seedling obtained from crossing Circus with Sweet Talk, in the following ways:

(1) The flowers of this new variety have as many as thirty-eight petals plus as many as fifteen petaloids, whereas the flowers of the pollen parent were semi-single to semi-double in petalage, never having more than twelve petals.

(2) The plants of the new variety are less spreading in growth habit than the plants of the pollen parent, and although the foliage of the new variety is also dark green, it is not as dull as the foliage of the pollen parent.

(3) In the new variety, the petals are so disposed as to obscure the stamens to some extent, whereas in the pollen parent the stamens are quite conspicuous.

(4) The flowers of this new variety are brilliant greenish-yellow, and retain this color to a notable degree, whereas the flowers of the pollen parent were nearer buff yellow, approaching Moderate Orange Yellow 7.5R 8/8, were conspicuously lacking in brilliance, and faded rather quickly after opening.

The new variety was asexually reproduced by budding in a garden in Chino, Calif. It has not yet been introduced to the trade.

The plant holds its distinguishing characteristics through succeeding propagations. These include its nearly continuous blooming during the growing season, the penetrating fragrance of the blooms, which is somewhat similar to anise, and the tendency to bear its flowers in clusters, although some are borne on single stems. The clusters have an irregular, more or less flat shape, on normal to strong stems of short to medium length. The blooms hold their color very well for several days after opening.

The plant is free blooming outdoors.

Details with respect to the plant and its bloom are as follows:

Bud: The peduncle is of medium length and medium caliper, usually erect, and medium green in color. It is generally smooth, except for a few small stipitate glands.

Before the calyx breaks, the bud is rather large for the floribunda class and is short and pointed, with a conspicuous neck. It has small foliaceous appendages on its surface, but these rarely extend beyond the tip of the bud. The color at this stage is medium to deep green.

As the calyx breaks the color approaches Brilliant Yellow Green 2.5GY 9/8, according to the Nickerson Color Fan, which is used throughout this specification to identify colors and shades which are not sufficiently indicated by their more common names.

As the first petal opens, the bud, which, as mentioned, is rather large for its class, is short and either pointed or urn-shape. The outside color ranges from Vivid Greenish Yellow 7.5Y 8/12 to Brilliant Greenish Yellow 7.5Y 9/8. Inside the bud the color is Vivid Greenish Yellow 7.5Y 8/12 at the base, but in the upper portion it varies from Brilliant Greenish Yellow 7.5Y 9/8 to a yellowish white. The first named color is the more common. The buds open up well.

Bloom: When the flower is fully open, the bloom is large for its class, ranging from 3" to 3½" generally and occasionally slightly larger. The petalage is double, but the stamens are not hidden. There may be from thirty to thirty-eight petals, usually arranged fairly regularly, but occasionally somewhat irregularly placed. In addition to the petals, there are several petaloids, sometimes as many as fifteen. The over-all form of the bloom is high-centered at first, becoming somewhat flatter at maturity. The petals are at first loosely roller outward, but at maturity they become more tightly rolled outwards, along their lateral margins.

Petals: The petals are moderately thick, with velvety texture inside and satiny texture outside. The outer petals are slightly broader than long, with the apex usually flat, and occasionally having a single notch. The intermediate petals are obovate in shape with the apex usually acute. The inner petals are narrowly obovate to nearly cuneate, irregularly scalloped, with an indistinct apex.

The following description of a flower, newly opened in September, refers to a rose grown outdoors at Chino, Calif.

The coloration of the petals on their outer surfaces was generally close to Brilliant Yellow 5Y 9/9. On the inner petals a slight greenish streak following the midrib was noted. On the intermediate petals the color was substantially uniform, and on the outer petals it was slightly diluted with white. The coloration of the petals on their inner surfaces was generally near to Brilliant Greenish Yellow 7.5Y 9/8. The shading was somewhat more intense on the lower portion of the inner, intermediate and outer petals, being especially so in the area of the veins and midrib of the inner surface of the outer petals.

The following description was made from a rose that was open for three days outdoors in the month of September.

The petals displayed a coloration which was a blend of white and Brilliant Yellow 5Y 9/9 on their outer surfaces, and a blend of white and Brilliant Greenish-Yellow 7.5Y 9/8 on their inner surfaces. In the outer petals the white was more prominent in the upper portions of the petals while the yellower tones were stronger in the basal areas, on both the inner and the outer surfaces. In the inner petals, the coloration was more nearly uniform over the petal area, the yellower color predominating on both the inner and outer surfaces.

The general color effect of the newly opened flower was near Brilliant Greenish-Yellow 7.5Y 9/8, whereas after three days the color was near Brilliant Yellow 5Y 9/9.

The petals drop off cleanly, but the petaloids persist. The longevity of the flowers is about four days, at least in the month of September, with respect to blooms on the bush in the garden. Cut roses grown outdoors, but kept at living room temperatures, will likewise last for about four days in the month of September.

*Reproductive organs*

Stamens: Medium in quantity, arranged more or less regularly about the pistils, and mixed with petaloids.

Filaments: Medium length, yellow, many without fertile anthers.

Anthers: Small, yellow, opening at various times.

Pollen: Sparse, and yellow in color.

Pistils: Few to medium in number.

Styles: Uneven, from medium length to long, varying in caliper, and quite red in the upper portion.

Stigma: Yellow.

Ovaries: All enclosed in calyx, or very nearly so.

Hips. Short, globular, usually without a conspicuous, neck, yellow-russet color at maturity with thick fleshy walls.

Sepals: Permanent, moderately short and recurved in shape, not distinctively colored.

Seeds: Variable in quantity, usually 6 to 15, rather large for class.

*Plant*

Foliage: The leaves, which are normal in quantity and compound in form, have from 3 to 5 leaflets. They are of medium size and moderately heavy-leather texture. As to the leaflets, the laterals are ovate, with terminals slightly ovate-lanceolate, and with apices acuminate.

The base is round, and the margins are simply serrated.

In the mature plant, the upper leaf surfaces are dark green and the under surfaces grey green, but the veins are dark olive green. In the young plant the upper surfaces are dark green, with the veins, reticulations and serrations a glossy purplish-red. The under surface is bright yellowish-green, but dominated by purplish-red veins, reticulations and serrations.

The supporting stem of the compound leaf, or rachis, is of light to medium weight. Its upper side is grooved, and sparsely lined with thin stipitate glands. Its under side is sparsely prickly, usually with 3 to 5 prickles.

The stipules are moderately short and moderately narrow, with short points, turning out at an angle of about 45°.

When compared to other varieties of roses grown under comparable garden conditions at Chino, Calif., this new variety has shown substantially better than average resistance to powdery mildew.

Growth: The plant is of dwarf habit, bushy, and is much branched. The growth is moderate to free, and the canes are of medium caliper.

The main stems are dull yellow green. They carry many large gray-brown prickles which are of medium length and of medium-length narrow base. Some prickles are straight and others slightly hooked downward. The main stems also carry a few small prickles, which also are gray-brown in color. There are no hairs.

The branches are dull yellow-green and carry many large and just a few small prickles. The prickles on the branches are brown in color and of the same shape as those on the main stems. There are no hairs.

The new shoots are green with reddish overlay, especially at the margins. They carry many large prickles which are long and straight with medium length narrow base. The prickles are green at the tip and reddish purple at the base. There are also a few small green prickles, but no hairs.

The leaves of the new variety are characteristically slightly rolled downwardly along their lateral margins, and are between 20% and 30% smaller, both in length and width, than the leaves of the seed parent, which latter, incidentally, are generally rather flat.

We claim:

1. A new and distinct variety of rose plant of the floribunda class, substantially as herein shown and described, characterized particularly as to novelty by the low-growing, relatively compact form of the plant and its nearly continuous blooming, during the growing season; the large size of its blooms, and their bright greenish-yellow coloration, together with the persistence of that coloration in the opened flowers; and the development of the flower from a short-pointed urn-shaped bud through a high-centered opening stage to the full bloom, which has double petalage but does not completely hide the stamens.

No references cited.

ROBERT E. BAGWILL, *Primary Examiner.*